(12) United States Patent
Shahzad et al.

(10) Patent No.: US 8,677,829 B2
(45) Date of Patent: Mar. 25, 2014

(54) APPARATUS, SYSTEMS AND METHODS FOR PRODUCTION AND INTEGRATION OF COMPACT ILLUMINATION SCHEMES

(75) Inventors: Khalid Shahzad, Shrub Oak, NY (US); Ladislav Jankovic, Fishkill, NY (US)

(73) Assignee: Koninklijke Philips N.V., Eindhoven (NL)

( * ) Notice: Subject to any disclaimer, the term of this patent is extended or adjusted under 35 U.S.C. 154(b) by 520 days.

(21) Appl. No.: 12/738,020

(22) PCT Filed: Oct. 13, 2008

(86) PCT No.: PCT/IB2008/054194
§ 371 (c)(1),
(2), (4) Date: Apr. 14, 2010

(87) PCT Pub. No.: WO2009/050632
PCT Pub. Date: Apr. 23, 2009

(65) Prior Publication Data
US 2010/0229650 A1    Sep. 16, 2010

Related U.S. Application Data

(60) Provisional application No. 60/980,207, filed on Oct. 16, 2007.

(51) Int. Cl.
*G01H 9/00* (2006.01)
*G02B 27/14* (2006.01)

(52) U.S. Cl.
USPC .............. 73/655; 359/629; 359/485; 359/495

(58) Field of Classification Search
USPC ........................................................ 73/655
See application file for complete search history.

(56) References Cited

U.S. PATENT DOCUMENTS

| | | | |
|---|---|---|---|
| 4,255,971 A | 3/1981 | Rosencwaig | |
| 5,070,733 A | 12/1991 | Nagata | |
| 5,840,023 A | 11/1998 | Oraevsky | |
| 5,977,538 A | 11/1999 | Unger | |
| 6,212,421 B1 | 4/2001 | Vo-Dinh | |
| 6,490,470 B1 | 12/2002 | Kruger | |
| 6,833,540 B2 | 12/2004 | MacKenzie | |
| 6,846,288 B2 | 1/2005 | Nagar | |
| 6,921,366 B2 | 7/2005 | Jeon | |
| 6,979,292 B2 | 12/2005 | Kanayama | |
| 2003/0025842 A1* | 2/2003 | Saccomanno | 348/758 |
| 2004/0174591 A1 | 9/2004 | Sander | |

OTHER PUBLICATIONS

Neiderhauser, Joel et al., Combined Ultrasound and Optoacoustic System for Real-Time High-Contrast Vascular Imaging in Vivo, Apr. 2003, IEEE Transactions on Medical Imaging, vol. 24, No. 4, 436-440.*

(Continued)

*Primary Examiner* — Hezron E Williams
*Assistant Examiner* — Gregory J Redmann

(57) ABSTRACT

Apparatus, systems and methods are provided for production and integration of compact illumination schemes. More particularly, disclosed embodiments relate to apparatus/systems and methods for production of highly compact illumination schemes, whereby photoacoustic waves are induced in a target sample. Additionally, the disclosed apparatus/systems and methods are effective to produce compact and portable integrated transducer-illumination arrays. Apparatus disclosed generally include at least one lighting source and a beamsplitting assembly. Systems disclosed generally include one or more apparatus for the production of compact lighting schemes, an ultrasonic transducer assembly and means for coupling the one or more apparatus and US transducer assembly with a target sample.

12 Claims, 5 Drawing Sheets

(56) References Cited

OTHER PUBLICATIONS

Neiderhauser, Joel et al., Combined Ultrasound and Optoacoustic System for Real-Time High-Contrast Vascular IMaging in Vivo, Apr. 2003, IEEE Transactions on Medical Imaging, vol. 24, No. 4, 426-440.*

Park, S. et al "Integrated System for Ultrasonic, Photoacoustic and Elasticity Imaging" Department of Biomedical Engineering, Univ. of Texas.

Wygant, I.O. et al Photoacoustic Imaging Using a Two-Dimensional CMUT Array IEEE Ultrasonics Symposium, 2005, pp. 1921-1924.

Niederhauser, Joel J. et al "Combined Ultrasound and Optoacoustic System for Real-Time High-Contrast Vascular Imaging in Vivo" IEEE Transactions on Medical Imaging, vol. 24, No. 4, Apr. 2005, pp. 436-440.

Oraevsky et al "Optoacoustic Tomography", Biomedical Photonics Handbook, p. 34-1, 2003.

Wang, Lihong V. "Ultrasound-Mediated Biophotonic Imaging: A Review of Acousto-Optical Tomography and Photo-Acoustic Tomography" Disease Makers, vol. 19, 2003-2004, pp. 123-138.

* cited by examiner

APPARATUS, SYSTEMS AND METHODS FOR
PRODUCTION AND INTEGRATION OF
COMPACT ILLUMINATION SCHEMES

BACKGROUND

1. Technical Field

The present disclosure is generally directed towards the field of photoacoustic (PA) imaging. More particularly, exemplary embodiments of the present disclosure are directed towards apparatus, systems and methods for the production of highly compact illumination schemes whereby PA waves are induced. Exemplary embodiments of the present disclosure are also directed towards apparatus, systems and methods for the production of a compact and portable, integrated transducer-illumination array (TIA).

2. Background Art

Photoacoustic (PA) imaging is a non-invasive medical imaging technique that may be used for detecting vascular and dermatological diseases, e.g., skin and breast cancers. The PA effect (as first reported in 1880 by A. G. Bell) arises wherein a target sample becomes heated due to absorption of light, producing an increase in pressure and/or volume of the material and its surroundings. By modulating the intensity of the light, the resulting periodic variation in pressure and/or volume can be detected as ultrasonic (US) waves. The US waves can ultimately be converted to near-real time two or three-dimensional images of the target sample using various mathematical equations. Thus, PA imaging provides relatively inexpensive and effective near real-time high-contrast imaging with relatively little danger to the target sample.

Prior apparatus, systems, and methods for PA imaging generally employ a single low-energy near-infrared laser to illuminate the target sample using a single US transducer. See, for example, "Optoacoustic Tomography," Oraevsky and Karabutov, Biomedical Photonics Handbook, P 34-1, 2003, CRC Press LLC, "Ultrasound-mediated biophotonic imaging: A review of acousto-optical tomography and photoacoustic tomography," Disease Makers 19, P. 123-138 (2003-2004); U.S. Pat. No. 4,255,971 to Rosencwaig, "Thermoacoustic Microscopy;" U.S. Pat. No. 5,070,733 to Nagata and Koda, "Photoacoustic Imaging Method;" U.S. Pat. No. 5,840,023 to Oraevsky et al., "Optoacoustic Imaging for Medical Diagnosis;" U.S. Pat. No. 6,212,421 to Vo-Dinh et al., "Method and Apparatus of Spectro-Acoustically Enhanced Ultrasonic Detection for Diagnostics;" U.S. Pat. No. 5,977,538 to Unger and Wu, "Optoacoustic Imaging System;" U.S. Pat. No. 6,979,292 to Kanayama et al., "Method and Apparatus for Forming an Image that shows information about a subject;" U.S. Pat. No. 6,833,540 to MacKenzie et al., "System for measuring a biological parameter by means of photoacoustic interaction;" and U.S. Pat. No. 6,846,288 to Nagar et al., "Photoacoustic Assay and Imaging System."

Of note, prior art teachings do not provide adequate means for selectively illuminating a target sample under a US transducer array. For example, Niederhauser et. al. disclose a glass prism illumination scheme for a US transducer array that is not sufficiently compact and/or portable and therefore not very practical for in-field PA imaging applications. [See, Niederhauser et. al., IEEE Transactions on Medical Imaging, Vol. 24, No. 4, Page 436, April 2005.] Additionally, existing illumination schemes do not enable control of illuminated patterns or geometries and/or to match the disparate illumination patterns and geometries with various transducers/transducer arrays on the market.

Generally, apparatus, systems and methods are needed that produce/provide compact illumination schemes. Furthermore, apparatus, systems and methods are needed that produce/provide compact illumination schemes of controllable patterns and/or geometries. Indeed, production of dynamically controllable illumination schemes would be particularly advantageous. Additionally, there is a need for apparatus, systems and methods that compactly integrate such illumination schemes with one or more ultrasonic transducers/ultrasonic transducer arrays.

These and other needs are satisfied by the disclosed apparatus, systems and methods described herein.

SUMMARY OF THE DISCLOSURE

Advantageous apparatus, systems and methods for the production and integration of compact illumination schemes are provided according to the present disclosure. Exemplary embodiments of the disclosed apparatus, systems and methods provide simple, effective and compact means for controllably illuminating a target sample for photoacoustic (PA) imaging purposes. However, while exemplary embodiments and implementations of the present disclosure generally relate to PA imaging, it is specifically contemplated that the disclosed apparatus, systems and methods apply to any field where compact illumination schemes may be used.

Exemplary embodiments of the presently disclosed apparatus/system generally include at least one lighting source and a beam splitting assembly. The at least one lighting source generally includes a laser optically configured to produce a concentrated beam of electromagnetic waves (e.g., visible or infrared light) of a desired intensity and wavelength. For PA imaging purposes, a wavelength in the near-infrared range is often desirable. The near-infrared wavelengths suffer less absorption and increased penetration deeper into a target sample, resulting in a larger radiated area and, ultimately, greater depths. The intensity of the laser beam is kept well within the required limits set by the official standards (ANSI limits). With reference to the polarizing beamsplitter that is generally associated with the disclosed apparatus/system, the degree of polarization of the source beam (e.g., homogenized and depolarized light) may have a significant impact on operation thereof. In exemplary embodiments of the present disclosure, the beamsplitting assembly generally includes a sequence of one or more beamsplitters, e.g., beamsplitter cubes, dicroic mirrored prisms, half silvered mirrors, dielectric optical coated mirrors and/or polarizers, such as Wollaston prisms. The sequence of one or more beamsplitters is typically configured such that the source beam for a subsequent beamsplitter is one of the resulting beams from a preceding beamsplitter.

The sequence of one or more beamsplitters is typically unbranched with each intermediate beamsplitter producing (i) a source beam for the subsequent beamsplitter, and (ii) an illumination beam. It is, however, specifically contemplated that branched configurations may likewise be employed, i.e., wherein a beamsplitter produces source beams for more than one subsequent beamsplitter. Therefore, in general, each disclosed beamsplitter produces at least two resultant beams including any combination of (i) one or more source beams for subsequent beamsplitters and/or (ii) one or more illumination beams.

In exemplary embodiments of the present disclosure, transmit-reflect ratios (T/R) are assigned to each beam splitter. Transmit-reflect ratios are relative measures of intensity and are defined, for purposes of the present disclosure, as the intensity of the light transmitted divided by the intensity of the light reflected (i.e., the intensity of a resulting source beam divided by the intensity of a resulting illumination beam). For beamsplitters that produce/yield more than two resultant beams, the transmit-reflect ratio is calculated for each resultant beam as the intensity of a particular resultant beam divided by the summed intensities of the remaining resultant beams. In general, transmit-reflect ratios can be used according to the present disclosure to calculate the relative intensities for each illumination beam in an entire sequence of one or more beamsplitters.

In exemplary embodiments of the present disclosure, the beamsplitting assembly includes at least one polarizing beamsplitter. The at least one polarizing beamsplitter (e.g., Wollaston prism) is generally effective to reflect waves of a particular polarization while transmitting waves of opposed polarizations. Thus, the intensity and polarization of resultant beams can be predictably controlled by properly configuring the polarizing beamsplitter. It is noted that, for a polarizing beamsplitter, the degree of polarization of the source beam is an essential element in determining the relative intensities of the resultant beams. For example, if an unpolarized light source is passed through a particular polarizing beamsplitter, the resultant S and P polarized beams may be of equal intensity if the T/R ratio is unity. By contrast, an S dominated polarized light source will produce a resultant S beam of greater intensity than the resultant P beam. In exemplary embodiments of the present disclosure, the beamsplitting assembly includes at least one polarizing beamsplitter that includes a dynamically switchable polarization material that supports and/or facilitates dynamic control of the resultant beam intensities and/or polarizations.

In exemplary embodiments of the present disclosure, the transmit-reflect ratios and/or sequence configurations of the one or more beamsplitters are selected and/or designed such that the resulting illumination beams are of desired intensities and/or are arranged in desired patterns/geometries, e.g., four illumination beams of increasing intensity arranged in line. In polarizing beamsplitting embodiments/implementations, the polarization of particular illumination beams can be similarly controlled. Moreover, where the at least one polarizing beamsplitter is dynamically controllable, the resultant beam intensities, geometrical arrangement and/or degrees of polarization can likewise be dynamically controlled.

As a result, the apparatus, systems and methods of the present disclosure advantageously provide adaptable imaging system that can be configured in near-real time for particular image requirements, e.g., scanning depth, sample material, etc. Direction-altering mirror assemblies may also be utilized prior to, during or after the beamsplitting process to alter the path of a beam and thus affect a particular pattern/geometry and/or assist in compacting the overall apparatus/system.

Advantageous systems and methods for the production and/or integration of compact illumination schemes are also provided according to the present disclosure. Exemplary embodiments generally include: (1) one or more components/apparatus for production of compact lighting schemes (i.e., illumination component(s)), (2) an ultrasonic (US) transducer assembly, and (3) means for coupling the illumination component(s) and US transducer assembly with a target sample. Coupling means/techniques may include, but are not limited to, use of (i) a US gel pad, e.g., a transparent ultrasound coupling pad, (ii) a container encasing the transducer assembly and illumination component(s) in coupling fluid, and/or (iii) US coupling gel.

In general, the disclosed illumination apparatus acts to illuminate specific regions of the target sample probing a desired region of interest for the PA effect. The resulting US waves emanating from the target sample are then detected using the disclosed transducer assembly. In exemplary embodiments, the disclosed apparatus/system may be integrated into a larger system, e.g., whereby data from the transducer assembly may be used to create two or three-dimensional images of the target sample. Of note, an additional feedback loop may be added using the image data to optimize the lighting, e.g., in embodiments/implementations where dynamic control is provided and/or facilitated.

In alternative exemplary embodiments and for compacting purposes, the at least one lighting source disclosed herein need not be part of an actual transducer assembly/illumination apparatus complex. Rather, the at least one lighting source, e.g., a laser, can be housed elsewhere, i.e., remote from the transducer/illumination complex, with the source beam introduced into the illumination apparatus via fiberoptics or other electromagnetic wave conduction mechanisms. The waveguide fiber may be advantageously tapered into the beam splitting assembly and encased therewith or otherwise bonded with respect thereto.

The disclosed illumination apparatus may be positioned relative to the transducer assembly such that the area and/or the target sample positioned directly under the transducer assembly is illuminated. A light reflecting layer, e.g., a mirror or foil, may be positioned between the transducer assembly and the target sample. In such embodiments/implementations, the reflective layer generally acts to minimize electromagnetic wave dissipation from the sample and illuminating the transducer. Additionally, the reflective layer may be coupled with one or more direction-altering mirror assemblies in order to minimize the distance between the transducer assembly and the target sample and/or to compact the system. For example, illumination beams emanating from the illumination apparatus could be reflected off of a mirror positioned directly below the illumination apparatus, e.g., wherein the mirror is angled such that the illumination beams are then reflected off of a second mirror and/or reflective layer toward the area of the target sample directly under the transducer assembly.

Additional advantageous features, functions and benefits associated with the disclosed apparatus, systems and methods will be apparent from the description which follows, particularly when read in conjunction with the accompanying figures.

BRIEF DESCRIPTION OF THE DRAWINGS

To assist those of ordinary skill in the relevant art in making and using the subject matter hereof, reference is made to the appended drawings, wherein.

DESCRIPTION OF EXEMPLARY EMBODIMENTS

The disclosed apparatus, systems and methods provide means for producing and/or integrating compact lighting schemes. Indeed, exemplary embodiments of the present disclosure produce compact illumination schemes of dynamically controllable intensity, polarization, patterns and/or geometries and integrate such illumination schemes with one or more ultrasonic (US) transducers/ultrasonic transducer arrays.

Figure 1:
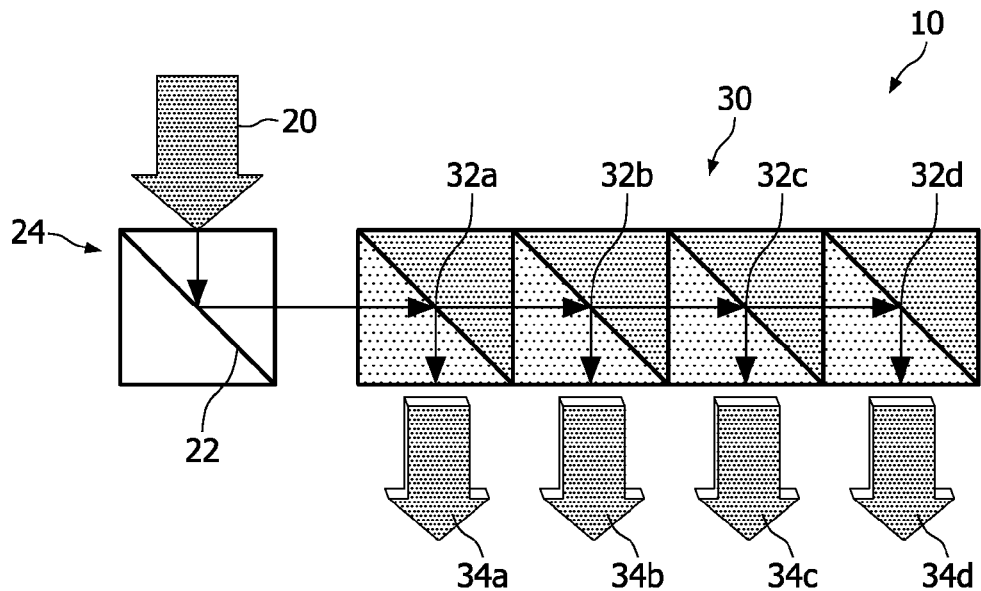
FIG. 1 depicts exemplary beamsplitting apparatus including four (4) non-polarizing beamsplitters with varying transmission-reflection coefficients.

With initial reference to FIG. 1, an exemplary apparatus for the production of compact lighting schemes (illumination apparatus) 10 is depicted that includes a single light source 20 and a beamsplitting assembly 30 of four non-polarizing beamsplitters 32a, 32b, 32c, and 32d with varying transmission-reflection (T/R) coefficients. The light source 20 is directed into the beamsplitting assembly 30 using a direction-altering mirror assembly 24 that includes a single angled mirror 22. The intensity of the resultant illumination beams 34a, 34b, 34c, and 34d is determined by the T/R coefficients.

Figure 2:
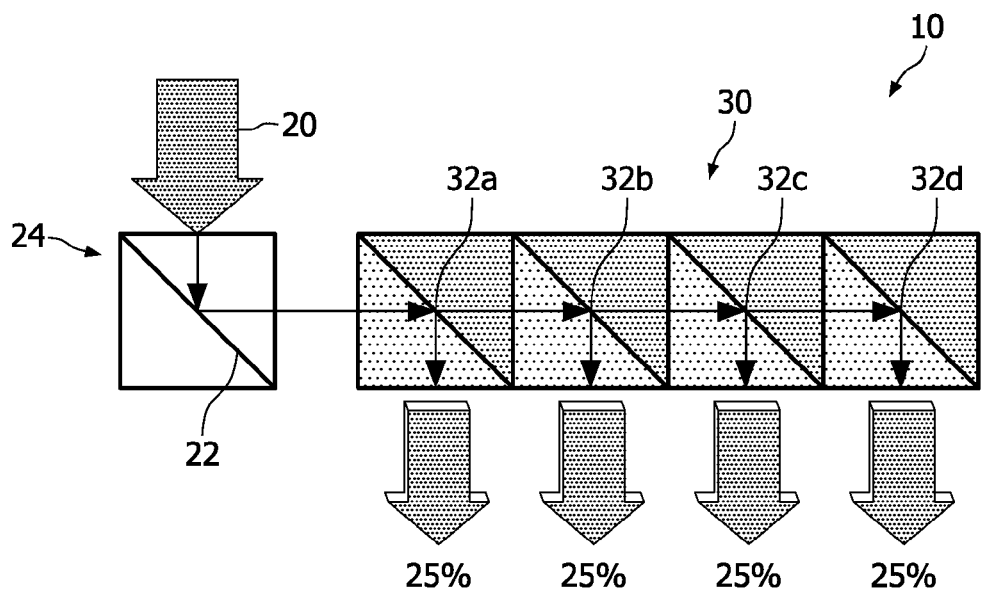
FIG. 2 depicts the exemplary beamsplitting apparatus of FIG. 1, wherein the transmission-reflection coefficients of the non-polarizing beamsplitters are configured such that a constant intensity lighting scheme is obtained.
Figure 3:
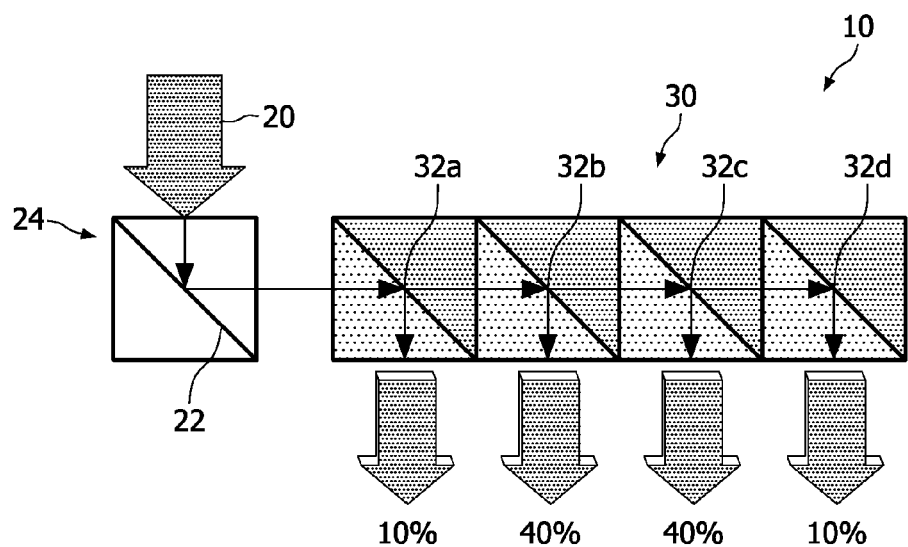
FIG. 3 depicts the exemplary beamsplitting apparatus of FIG. 1, wherein the transmission-reflection coefficients of the non-polarizing beamsplitters are configured such that a center-concentrated lighting scheme is obtained.
Figure 4:
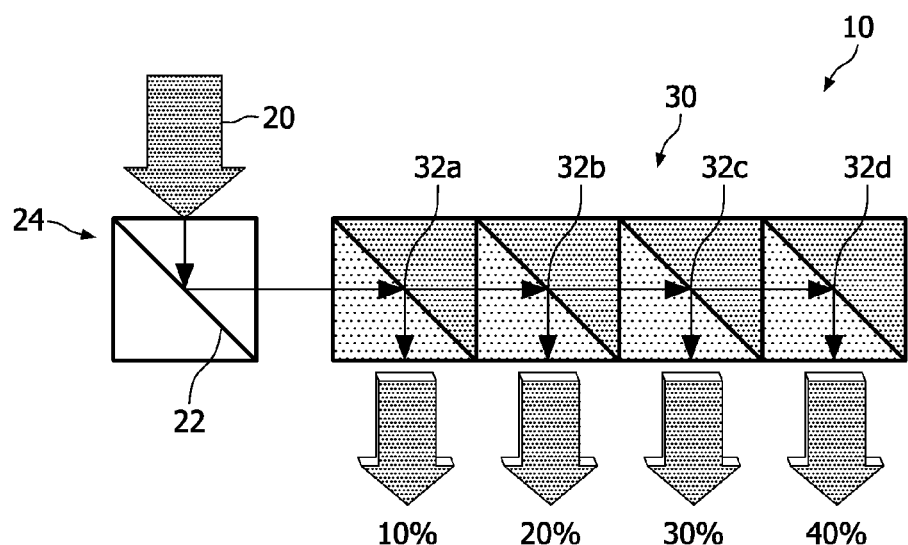
FIG. 4 depicts the exemplary beamsplitting apparatus of FIG. 1, wherein the transmission-reflection coefficients of the non-polarizing beamsplitters are configured such that a graduated intensity lighting scheme is obtained.

FIGS. 2-4 depict exemplary intensity configurations of the illumination beams 34a, 34b, 34c, and 34d for the exemplary apparatus 10 depicted in FIG. 1. More specifically, FIG. 2 depicts a uniform intensity scheme, FIG. 3 depicts a center focused intensity scheme, and FIG. 4 depicts a graduated intensity scheme. Each scheme is produced by using the correct T/R ratio for each beamsplitter 32a, 32b, 32c, and 32d. For example, the uniform intensity scheme depicted in FIG. 2 is produced using the following T/R ratios (assuming a source beam 20 intensity of 100): T/R for beamsplitter 32a=75/25, T/R for beamsplitter 32b=50/25, T/R for beamsplitter 32b=25/25, and T/R for beamsplitter 32c=0/25). The physical effect of these coefficients is that, for example, beamsplitter 32a produces a resultant illumination beam with an intensity of 25 and a resultant source beam for beamsplitter 32b with an intensity of 75. Similarly T/R ratios for the illumination schemes depicted in FIG. 3 and FIG. 4 can be calculated (once again assuming a source beam 20 intensity of 100) as follows: for the center focused intensity scheme (10/90, 40/50, 40/10, 0/10) and for the graduated intensity scheme (10/90, 20/70, 30/40, 40/0) (where the ratios are presented as T/R for beamsplitter 32a, T/R for beamsplitter 32b, T/R for beamsplitter 32c, T/R for beamsplitter 32d, respectively). Of note, since the final beamsplitter 32d effectively acts as a perfect mirror reflecting all the remaining light, such beamsplitter 32d may be replaced with a mirror assembly according to the exemplary implementation depicted therein.

Figure 5:
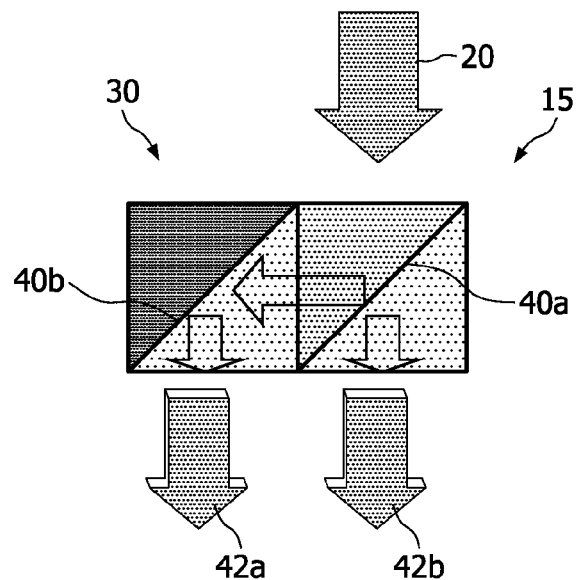
FIG. 5 depicts exemplary beamsplitting apparatus that includes a dynamic polarizing beamsplitter with varying polarization coefficients

With reference now to FIG. 5, an exemplary illumination apparatus 15 is depicted that includes a single light source 20 and a beamsplitting assembly 30 that includes two polarizing beamsplitters 40a and 40b with varying polarization effects. In exemplary embodiments of the present disclosure, the light source 20 is a homogenous non-polarized laser; however, alternative sources/polarizations may be utilized. As discussed previously, for apparatus/systems disclosed herein that include at least one polarizing beamsplitter, the polarization of the source light 20 is an essential element in determining the intensity and/or polarization of the resultant illumination beams 42a and 42b. Alternatively, the polarization of the source light 20 may be altered to dynamically and controllably effect a change in the resultant lighting scheme.

Figure 6:
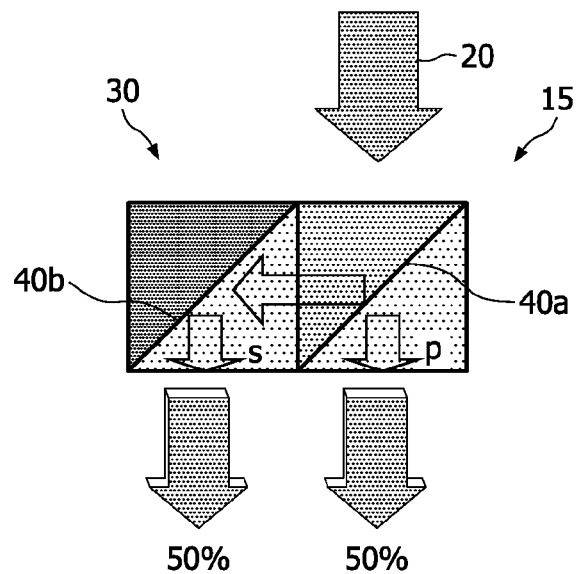
FIG. 6 depicts the exemplary beamsplitting apparatus of FIG. 5, wherein the dynamic polarizing beamsplitter is a two-stage polarizing beamsplitters, whereby homogenized and depolarized electro magnetic radiation (i.e., light) is split into S and P polarization beams of equal intensity.

In the exemplary embodiment depicted in FIG. 5, the second polarizing beamsplitter 42b effectively acts as a perfect mirror reflecting all the remaining light and may accordingly be replaced with a mirror assembly. FIG. 6 depicts an exemplary embodiment of the illumination apparatus 15 depicted in FIG. 5, wherein an unpolarized light source 20 is passed through the polarizing beamsplitters 40a and 40b in order to produce resultant S and P polarized illumination beams of equal intensity.

Figure 7:
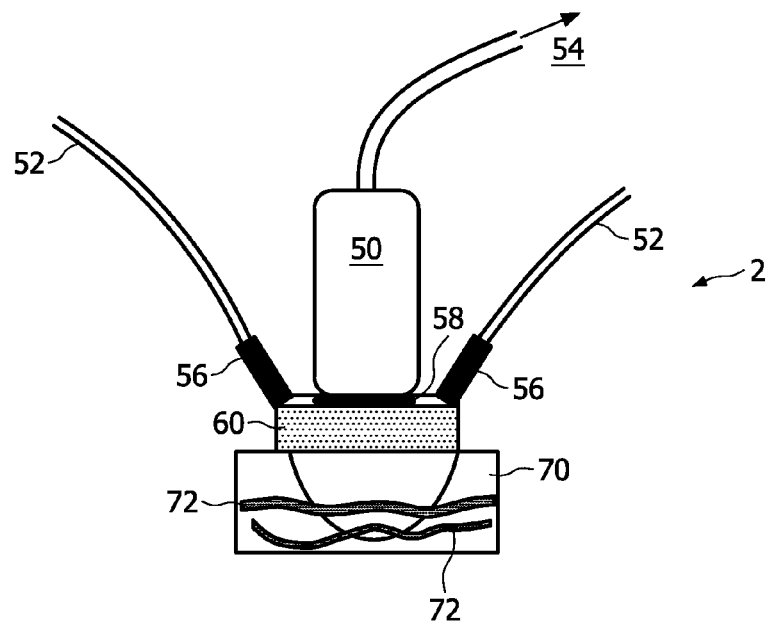
FIG. 7 depicts an exemplary integrated illumination-transducer system that includes a US gel pad and reflective foil.
Figure 8:
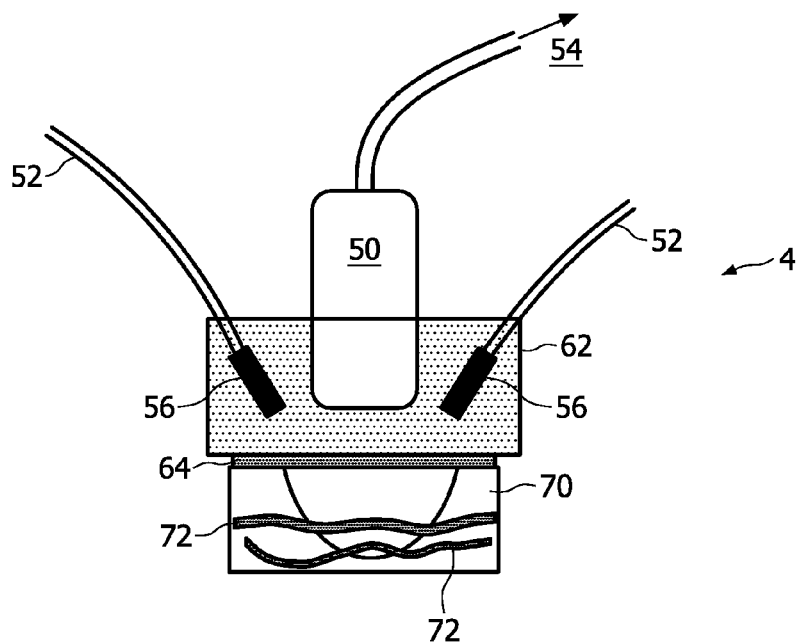
FIG. 8 depicts an exemplary integrated illumination-transducer system wherein beamsplitting apparatus are encased together with a transducer/transducer array in a container.
Figure 9:
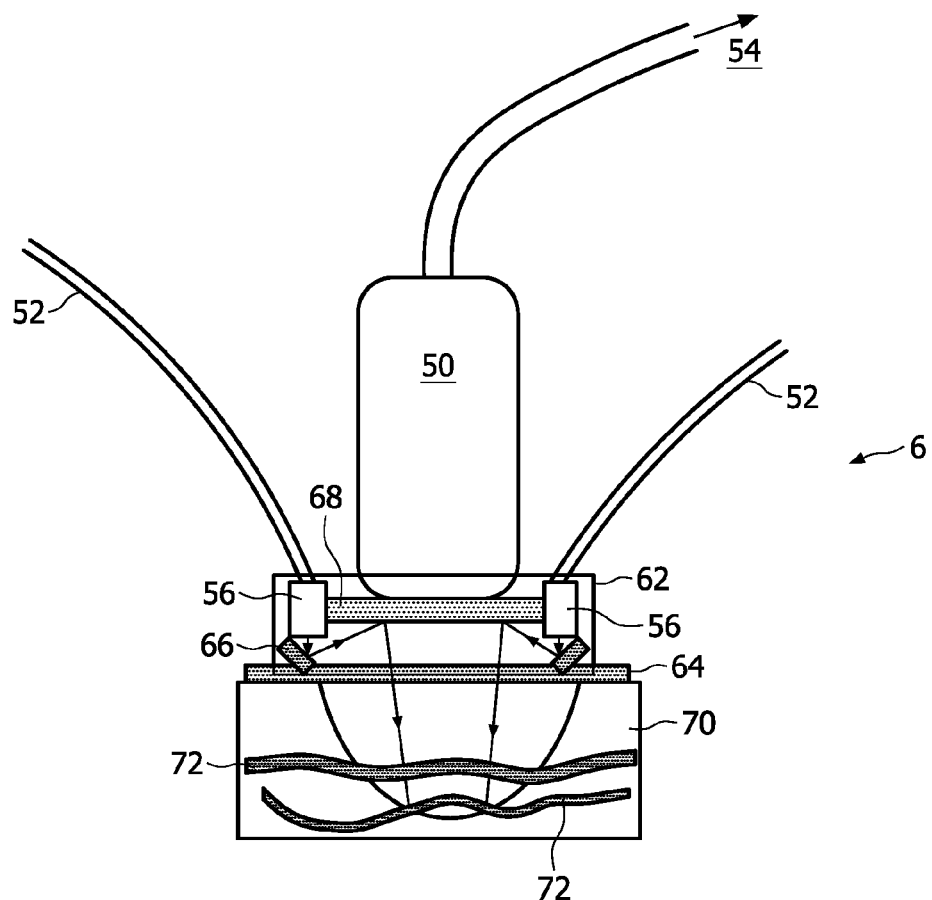
FIG. 9 depicts an exemplary integrated illumination-transducer system wherein a compact housing scheme is used to minimize the separation between a transducer/transducer array and a target sample.

FIGS. 7-9 depict various embodiments of systems for integrating compact lighting schemes of the present disclosure with a transducer/transducer array. Of note, the disclosed systems include: (1) one or more apparatus for the production of compact lighting schemes (i.e., illumination component(s)/apparatus) 56, (2) an ultrasonic (US) transducer assembly 50, and (3) means for coupling the one or more illumination component(s) 56 and US transducer assembly 50 with a target sample 70. In the exemplary embodiments depicted herein, the target sample 70 is a dermis layer of live patient wherein subsurface blood vessels 72 are being investigated for vascular disease. The source beams for the illumination apparatus, as depicted in the exemplary embodiments depicted in FIGS. 7-9, are introduced into the system via fiberoptic lines 52. The waveguide fiber 52 is tapered into the illumination apparatus 56 and encased therewith. Also, in the exemplary embodiments depicted in FIGS. 7-9, the disclosed systems 2, 4 and 6, respectively, are integrated into a larger system whereby data from the transducer assembly 50 is transmitted to a processing device 54, e.g., a computer, and used to create two or three-dimensional images of the target sample 70.

In exemplary embodiments of the present disclosure, the disclosed means for coupling illumination component(s) and US transducer assembly may include, but is not limited to, use of a US gel pad, use of a container encasing the transducer assembly and illumination apparatus in coupling fluid, and/or US coupling gel. FIG. 7 depicts the use of a transparent ultrasound gel coupling pad 60 as the means for coupling the illumination apparatus 56 and the transducer assembly 50 with the target sample 70. Alternatively, FIG. 8 and FIG. 9 depict the combined use of a container of coupling fluid 62 and a layer of US coupling gel 64 as means for coupling the exemplary system 4 with the target sample 70. It is noted that, in the particular embodiments depicted in FIG. 8 and FIG. 9, the illumination apparatus 56 and part of the transducer assembly 50 are encased in the container 62.

For the particular embodiments presented in FIGS. 7-9, the illumination apparatus 56 is positioned relative to the transducer assembly 50 such that the area and/or the target sample 70 positioned directly under the transducer assembly 50 is illuminated. For the particular embodiment depicted in FIG. 9, a reflective layer 68 is coupled with direction-altering mirrors 66 in order to minimize the distance between the transducer assembly 50 and the target sample 70, thus compacting the system 6. The illumination beams emanating from the illumination apparatus 56 are first reflected off the mirrors 66 and then reflected off the reflective layer 68 toward the area of the target sample 70 directly under the transducer assembly 50. A reflective layer may also be used as depicted in FIG. 7 to counteract the dissipation of electromagnetic waves from the sample. In exemplary system 2, the illumination beams emanating from the illumination apparatus 56 are further concentrated on the target sample 70 by means of the reflective layer 58 positioned under and adjacent to the transducer assembly 50.

Although the present disclosure is described with reference to exemplary embodiments and implementations thereof, the present disclosure is not to be limited by or to such exemplary embodiments and/or implementations. Rather, the apparatus, systems and methods of the present disclosure are susceptible to various modifications, variations and/or enhancements without departing from the spirit or scope of the present disclosure. Accordingly, the present disclosure expressly encompasses all such modifications, variations and enhancements within its scope.

The invention claimed is:

1. A system for compactly integrating an illumination apparatus with an ultrasonic transducer assembly, the system comprising:
   one or more illumination apparatus for the production of lighting schemes, the one or more illumination apparatus including (i) at least one lighting source configured to provide an illumination beam, and (ii) a beamsplitting assembly that includes a sequence of one or more beamsplitters of varying transmit-reflect ratios, wherein the sequence of one or more beamsplitters is configured such that a source beam for a subsequent beamsplitter of the sequence is one of the resulting beams from a preceding beamsplitter of the sequence, wherein the illumination beam of the at least one light source is passed through the beamsplitting assembly and wherein the beamsplitting assembly divides the illumination beam of the at least one light source into one or more beams of desired intensity before passing said beams relative to a target sample;
   an ultrasonic transducer assembly including at least one ultrasonic transducer, wherein said ultrasonic transducer assembly detects ultrasonic waves emanating relative to the target sample;
   a reflective layer coupled with one or more direction-altering mirror assemblies, wherein the reflective layer is positioned directly below the ultrasonic transducer assembly, wherein the one or more direction-altering mirror assemblies are positioned (i) directly below a respective beamsplitting assembly of the one or more illumination apparatus and (ii) below the ultrasonic transducer assembly, and wherein the one or more direction-altering mirror assemblies are angled such that the one or more beams of desired intensity emanating from the respective one or more illumination apparatus are then reflected off of the reflective layer toward the area of the target sample directly under the transducer assembly; and
   an acoustic couplant for coupling the one or more illumination apparatus for the production of compact lighting schemes and the ultrasonic transducer assembly with the target sample.

2. The system according to claim 1, wherein the acoustic couplant comprises an ultrasonic gel pad.

3. The system according to claim 1, wherein the acoustic couplant comprises a container with coupling fluid and a layer of ultrasonic gel.

4. The system according to claim 1, wherein the acoustic couplant comprises a housing and a layer of ultrasonic gel.

5. The system according to claim 1, wherein the ultrasonic transducer assembly comprises a transducer array.

6. The system according to claim 5, wherein one or more of the sequence of one or more beamsplitters includes at least one polarizing beamsplitter comprised of dynamically switchable polarization material, such that the resulting beam intensities and/or polarizations are dynamically controllable.

7. The system of claim 1, further wherein the illumination scheme comprises a center focused intensity scheme.

8. The system of claim 7, wherein the one or more illumination apparatus for production of compact lighting schemes comprises two illumination apparatus, wherein the beamsplitting assembly of each illumination apparatus comprises a sequence of four beamsplitters, and wherein the center focused intensity scheme includes intensities of 10, 40, 40, and 10 out of 100 percent intensity for respective beamsplitters of the beamsplitting assembly.

9. The system of claim 1, further wherein the illumination scheme comprises a graduated intensity scheme.

10. The system of claim 9, wherein the one or more illumination apparatus for production of compact lighting schemes comprises two illumination apparatus, wherein the beamsplitting assembly of each illumination apparatus comprises a sequence of four beamsplitters, and wherein the graduated intensity scheme includes intensities of 10, 20, 30, and 40 out of 100 percent intensity for respective beamsplitters of the beamsplitting assembly.

11. The system of claim 1, wherein the one or more beams of desired intensity are dynamically controlled to produce an illumination scheme configured to match with the at least one ultrasonic transducer of the ultrasonic transducer assembly.

12. A method for imaging a target sample, comprising:
   providing one or more illumination apparatus for the production of compact lighting schemes, the one or more illumination apparatus including (i) at least one lighting source configured to provide an illumination beam, and (ii) a beamsplitting assembly that includes a sequence of one or more beamsplitters of varying transmit-reflect ratios, wherein the sequence of one or more beamsplitters is configured such that a source beam for a subsequent beamsplitter of the sequence is one of the resulting beams from a preceding beamsplitter of the sequence, wherein the illumination beam of the at least one light source is passed through the beamsplitting assembly and wherein the beamsplitting assembly divides the illumination beam of the at least one light source into one or more beams of desired intensity before passing said beams relative to a target sample;
   providing an ultrasonic transducer assembly including at least one ultrasonic transducer; wherein said ultrasonic transducer assembly detects ultrasonic waves emanating relative to the target sample;
   providing a reflective layer coupled with one or more direction-altering mirror assemblies, wherein the reflective layer is positioned directly below the ultrasonic transducer assembly, wherein the one or more direction-altering mirror assemblies are positioned (i) directly below a respective beamsplitting assembly of the one or more illumination apparatus and (ii) below the ultrasonic transducer assembly, and wherein the one or more direction-altering mirror assemblies are angled such that the one or more beams of desired intensity emanating from the respective one or more illumination apparatus are then reflected off of the reflective layer toward the area of the target sample directly under the transducer assembly; and coupling the one or more illumination apparatus for the production of compact lighting schemes and the ultrasonic transducer assembly with the target sample.

* * * * *